US008133743B2

(12) United States Patent
Hui

(10) Patent No.: US 8,133,743 B2
(45) Date of Patent: Mar. 13, 2012

(54) PHENOBARBITAL DERIVATIVES USEFUL IN IMMUNOASSAY

(75) Inventor: Raymond Hui, Indianapolis, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 541 days.

(21) Appl. No.: 12/236,073

(22) Filed: Sep. 23, 2008

(65) Prior Publication Data
US 2009/0104713 A1 Apr. 23, 2009

Related U.S. Application Data

(60) Provisional application No. 60/981,202, filed on Oct. 19, 2007.

(51) Int. Cl.
G01N 33/532 (2006.01)
G01N 33/548 (2006.01)
C07D 239/64 (2006.01)

(52) U.S. Cl. ......... 436/544; 436/56; 436/529; 544/305

(58) Field of Classification Search .............. None
See application file for complete search history.

(56) References Cited

U.S. PATENT DOCUMENTS

| 4,255,566 A | 3/1981 | Carrico et al. |
| 4,279,992 A | 7/1981 | Boguslaski et al. |
| 4,363,874 A | 12/1982 | Greenquist |
| 4,543,412 A | 9/1985 | Flentge et al. |
| 4,614,823 A | 9/1986 | Kirkemo et al. |
| 5,096,838 A | 3/1992 | Grote et al. |
| 5,099,020 A | 3/1992 | Grote et al. |
| 5,284,948 A | 2/1994 | Ponticello et al. |
| 5,298,403 A | 3/1994 | Danielson et al. |
| 5,414,085 A | 5/1995 | Buechler |
| 5,601,994 A | 2/1997 | Oenick et al. |
| 5,618,926 A | 4/1997 | Salamone et al. |
| 6,472,227 B1 | 10/2002 | Adamczyk et al. |

FOREIGN PATENT DOCUMENTS

EP 0517327 B1 8/2001

OTHER PUBLICATIONS

Harmanson. Heterobifunctional Cross-linkers & Preparation of Hapten-carrier conjugates; 1996, pp. 228-286 & 519-455; Elsevier Science, Academic Press, San Diago, California 92101-4495, USA.*
Dean et al. Simultaneous determination of phenytoin and phenobarbital in serum or plasma by substreate-labeled fluorescent immunoassay. Clin. Chem. 1983, vol. 29, No. 6, pp. 1051-1056.*
Castro et al. Phenobarbital secific antibody production: preparation of 5-phenyl-5-(4-aminobutyl) barbituric acid-bovine albumin conjugate., Abstract, Res Commun Chem Pathol Pharmacol. 1990.*
Adamczyk, M. et al., "Linker-Mdeiated Modulation of the Chemiluminescent Signal from N10-(3-Sulfopropyl)-N-sufonylacridinium-9-carboxamide Tracers," Bioconjugate Chem 11 (2000) 714-724.

* cited by examiner

Primary Examiner — Shafiqul Haq

(57) ABSTRACT

Phenobarbital derivatives synthesized out of the alkyl chain at the 5-position, particularly with hydrophilic properties, and carrying an active ester at the end, allow formation of amino-dextran conjugates that give curves in the desired range of the assay in the ONLINE TDM microparticle assay format when matched against the Roche FPIA antibody specific for phenobarbital ("an antibody specific for phenobarbital").

4 Claims, 8 Drawing Sheets

PHENOBARBITAL DERIVATIVES USEFUL IN IMMUNOASSAY

RELATED APPLICATIONS

The present invention claims priority to provisional application U.S. Ser. No. 60/981,202 filed Oct. 19, 2007.

FIELD OF THE INVENTION

The present invention relates to the field of therapeutic drug monitoring and in particular to phenobarbital derivatives

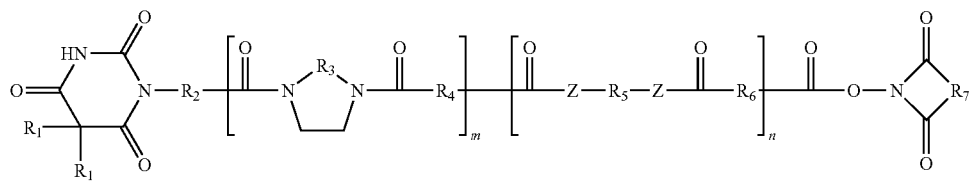

and assay methods using such derivatives for determining phenobarbital in a patient sample.

BACKGROUND OF THE INVENTION

The problem overcome by the present invention is development of an improved non-isotopic, homogeneous microparticle agglutination immunoassay specific for the therapeutic drug phenobarbital without cross-reactivity to other substances in the same class of drugs (barbiturates) based on the kinetic interaction of microparticles (KIMS).

Other non-isotopic immunoassays specific for phenobarbital have used different technologies such as fluorescence polarization immunoassay (FPIA), e.g., Kirkemo et al., U.S. Pat. No. 4,614,823; immunoassays with enzyme-mediated signal generation, e.g., Bogulaski et al., U.S. Pat. No. 4,279,992 (EIA); Flentge et al., U.S. Pat. No. 4,543,412 (EIA); Carrico et al., U.S. Pat. No. 4,255,566 (Flavin-phenobarbital derivatives for EIA); Greenquist, U.S. Pat. No. 4,363,874 (EIA on a membrane); Scholz et al., Recent Dev. Ther. Drug Monit. Clin. Toxicol., 1992, 375-381 (CEDIA); and chemiluminescent immunoassay, e.g., Adamezyk et al., Bioconjugate Chem., 2000, 11, 714-724 (5-position C6-OCONH—R derivatives), while other more esoteric methods have also been used.

There are assays for barbiturates as a class in which phenobarbital has cross-reactivity. (Adamczyk et al., U.S. Pat. No. 6,472,227 [using sec-butyl and cyclopentenyl barbiturate derivatives]; Grote & Hu, U.S. Pat. Nos. 5,099,020 and 5,096,838 [FPIA using 5,5-dialkylbarbiturate derivatives although a phenobarbital derivative is encompassed in the description and claims].

There is also a barbiturate-class microparticle agglutination immunoassay (U.S. Pat. No. 5,618,926) but with a secobarbital-BSA conjugate immobilized on microparticle (as opposed to the phenobarbital analog-aminodextran conjugate in solution format in the present invention). Phenobarbital is one of many with cross-reactivity in the assay.

Buechler (U.S. Pat. No. 5,414,085) describes barbiturate compounds including "5-aryl" substituted substances also synthesized out of the 5-position ending with a thiolactone terminus, although the teaching is directed towards secobarbital derivatives.

Phenobarbital derivatives leashed out of N1 of the barbiturate core, i.e., out of the nitrogen at position 1 rather than out of carbon at position 5 as is the case with compounds of the present invention, are revealed in U.S. Pat. No. 5,284,948, U.S. Pat. No. 5,298,403, EP 517327, and U.S. Pat. No. 5,601,994. See diagram below. The last cited patent also describes an enzyme immunoassay for barbiturates but exemplifies only phenobarbital and its derivatives without indication of crossreactivities of other barbiturates in the assay.

U.S. Pat. No. 5,284,948 and U.S. Pat. No. 5,298,403 also discuss binding of enzyme-labeled phenobarbital derivatives formed from the N1-derivatized substances shown above with antibodies immobilized on beads which are spun down/pelleted in a discrete step, while EP 517327 reveals an enzyme immunoassay using antibodies immobilized on a membrane.

SUMMARY OF THE INVENTION

It is against the above background that the present invention provides certain unobvious advantages and advancements over the prior art. In particular, the inventors have recognized a need for improvements in phenobarbital derivatives useful in immunoassay.

The inventors have found that phenobarbital derivatives synthesized out of the alkyl chain at the 5-position, particularly with hydrophilic properties and carrying an active ester at the end, allow formation of aminodextran conjugates that give curves in the desired range of the assay in the ONLINE TDM (Roche Diagnostics Operations, Inc.) microparticle assay format when matched against the Roche FPIA (fluorescence polarization immunoassay) antibody specific for phenobarbital ("an antibody specific for phenobarbital").

One embodiment of the present invention relates to a compound having the structure

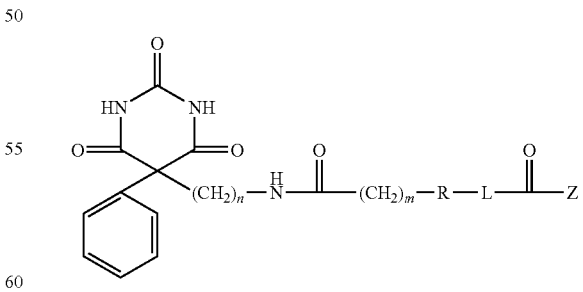

wherein n is 4-6, m is 1-4, R is —NHCO— or —CONH—, L is a linking group comprising 2-18 carbon atoms and 1-6 heteroatoms arranged in a straight or branched chain and containing up to 1 cyclic structure, provided that the first atom attached to R is carbon, and Z is a leaving group or a polysaccharide.

Another embodiment of the present invention relates to a compound having the structure

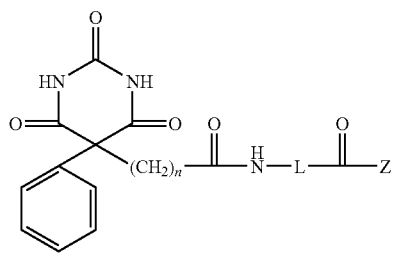

wherein n is 4-6, L is a linking group comprising 2-18 carbon atoms and 1-6 heteroatoms arranged in a straight or branched chain and containing up to 1 cyclic structure, provided that the first atom attached to —CONH— is carbon, and Z is a leaving group or a polysaccharide.

Another embodiment of the invention is a phenobarbital analog having the structure

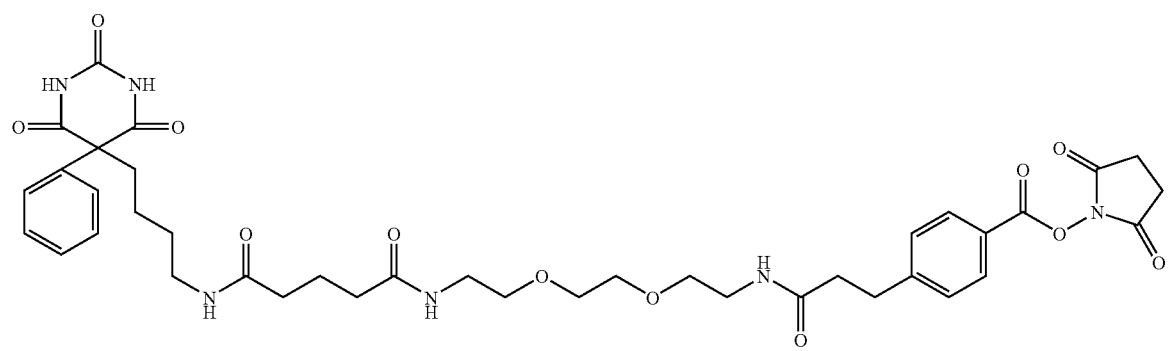

Another embodiment of the invention is a phenobarbital analog having the structure

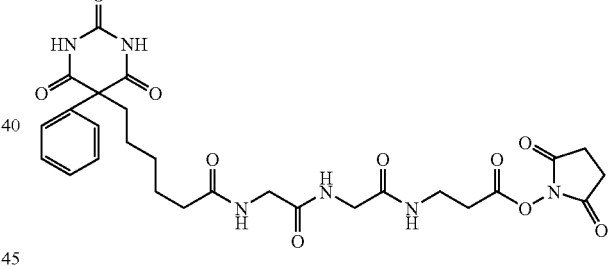

Another embodiment of the invention is a phenobarbital analog having the structure

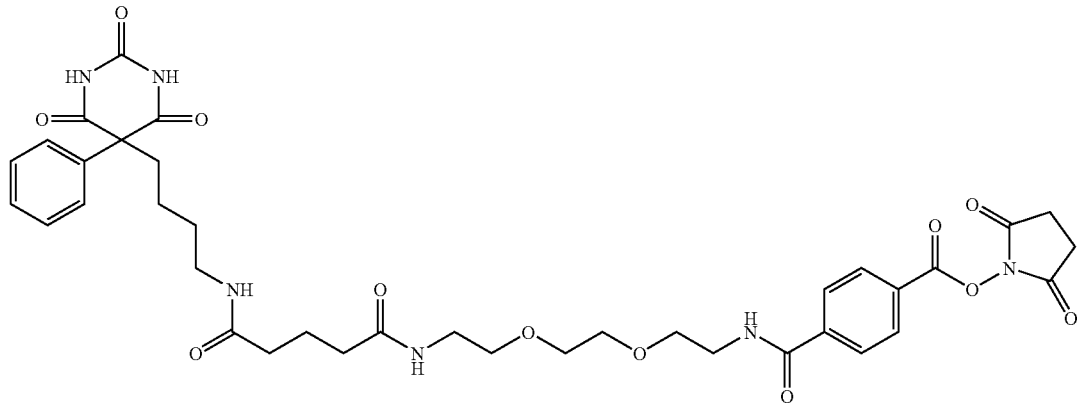

Another embodiment of the invention is a phenobarbital analog conjugate having the structure

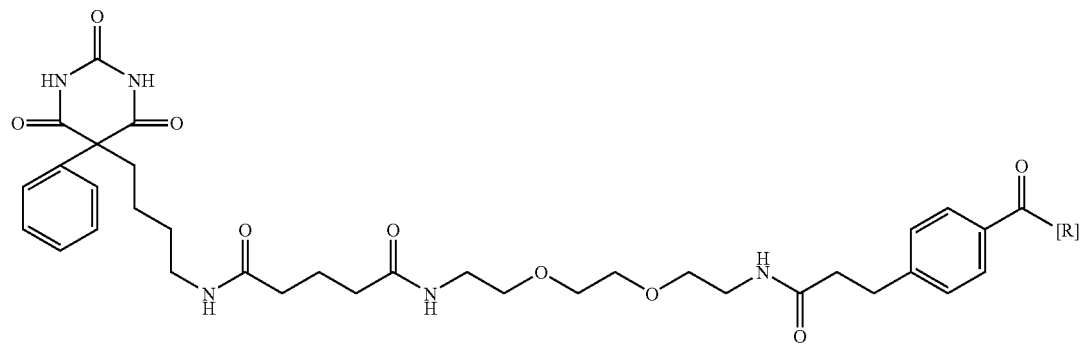

wherein R is aminodextran.

Another embodiment of the invention is a phenobarbital analog conjugate having the structure

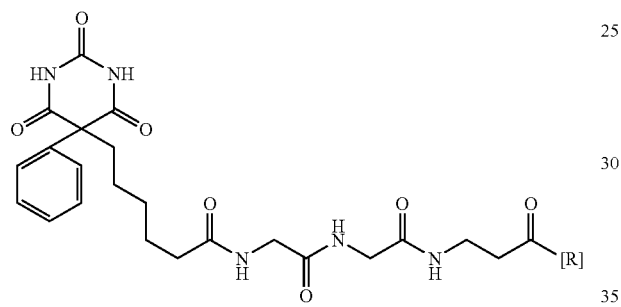

wherein R is aminodextran.

Another embodiment of the invention is a phenobarbital analog conjugate having the structure

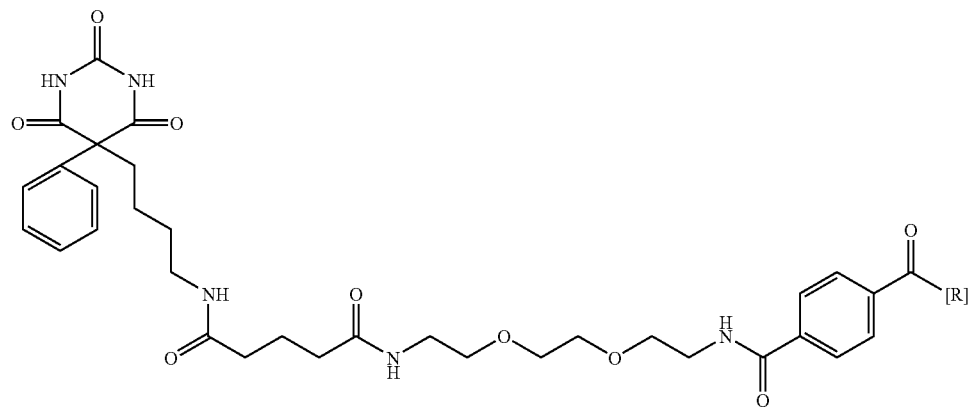

wherein R is aminodextran.

Another embodiment of the invention is a test kit for determining phenobarbital in a sample comprising in packaged combination antibody coated microparticles, wherein the antibody is specific for phenobarbital, instructions for performing the determination, and a phenobarbital analog conjugate according to the formula:

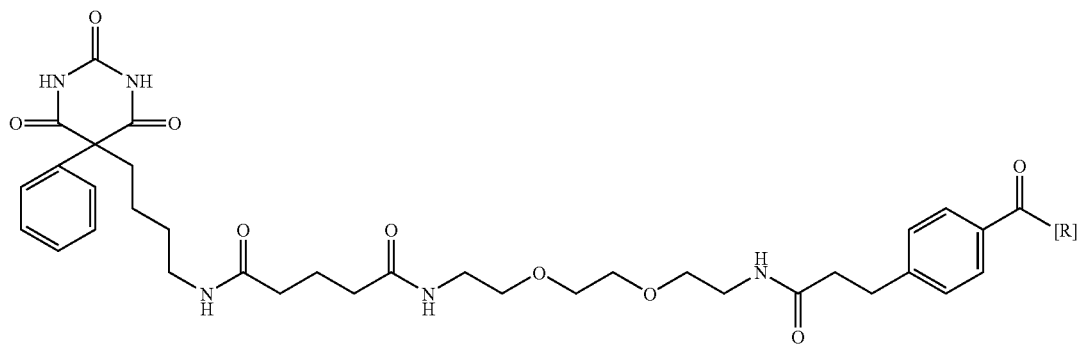

wherein R is aminodextran.

Another embodiment of the invention is a test kit for determining phenobarbital in a sample comprising in packaged combination antibody coated microparticles, wherein the antibody is specific for phenobarbital, instructions for performing the determination, and a phenobarbital analog conjugate according to the formula:

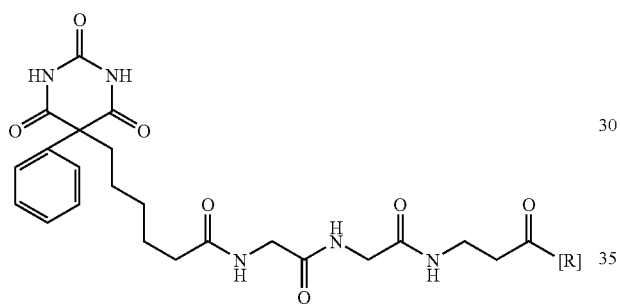

wherein R is aminodextran.

Another embodiment of the invention is a test kit for determining phenobarbital in a sample comprising in packaged combination antibody coated microparticles, wherein the antibody is specific for phenobarbital, instructions for performing the determination, and a phenobarbital analog conjugate according to the formula:

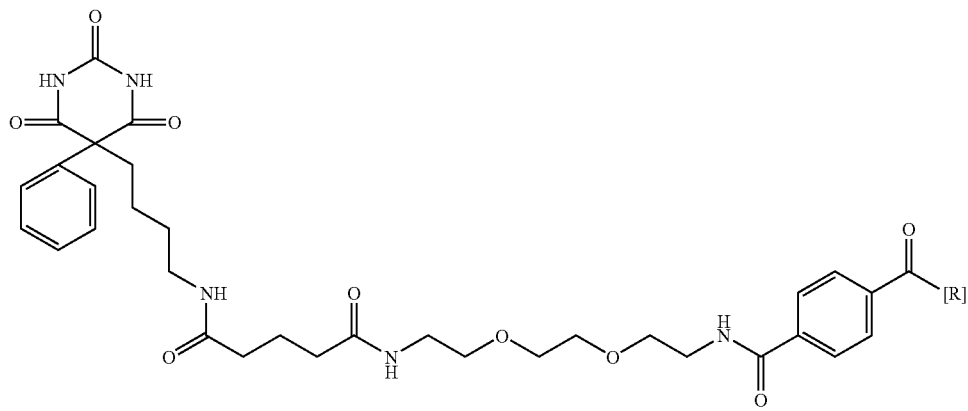

wherein R is aminodextran.

Another embodiment of the invention is an immunoassay method for determining the presence or amount of phenobarbital in a sample comprising the steps of: combining a sample suspected of containing phenobarbital with an antibody specific for phenobarbital and a phenobarbital analog conjugate, wherein the antibody is bound to microparticles, wherein the phenobarbital in the sample and the phenobarbital analog conjugate competitively bind to the antibody, and wherein binding of phenobarbital analog conjugate to the antibody-bound microparticles inhibits microparticle agglutination, and determining an amount of agglutination inhibition as a measure of the presence or amount of phenobarbital in the sample, wherein the phenobarbital analog conjugate has the structure

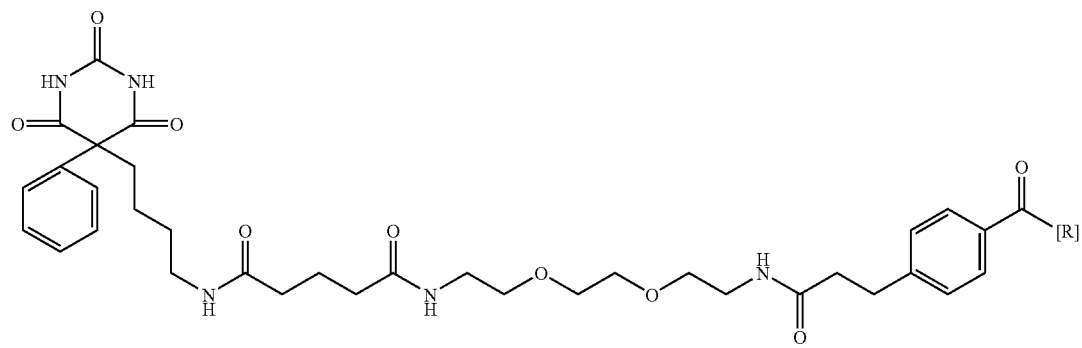

wherein R is aminodextran.

Another embodiment of the invention is an immunoassay method for determining the presence or amount of phenobarbital in a sample comprising the steps of: combining a sample suspected of containing phenobarbital with an antibody specific for phenobarbital and a phenobarbital analog conjugate, wherein the antibody is bound to microparticles, wherein the phenobarbital in the sample and the phenobarbital analog conjugate competitively bind to the antibody, and wherein binding of phenobarbital analog conjugate to the antibody-bound microparticles inhibits microparticle agglutination, and determining an amount of agglutination inhibition as a measure of the presence or amount of phenobarbital in the sample, wherein the phenobarbital analog conjugate has the structure

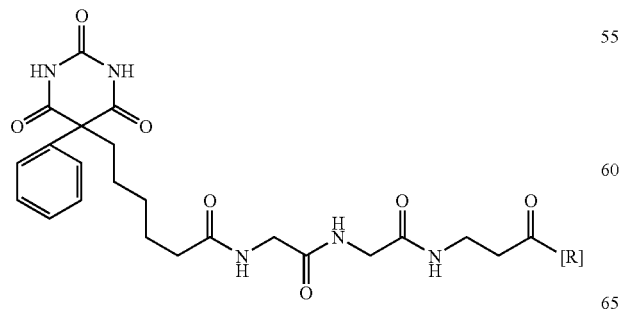

wherein R is aminodextran.

Another embodiment of the invention is an immunoassay method for determining the presence or amount of phenobarbital in a sample comprising the steps of: combining a sample suspected of containing phenobarbital with an antibody specific for phenobarbital and a phenobarbital analog conjugate, wherein the antibody is bound to microparticles, wherein the phenobarbital in the sample and the phenobarbital analog conjugate competitively bind to the antibody, and wherein binding of phenobarbital analog conjugate to the antibody-bound microparticles inhibits microparticle agglutination, and determining an amount of agglutination inhibition as a measure of the presence or amount of phenobarbital in the sample, wherein the phenobarbital analog conjugate has the structure

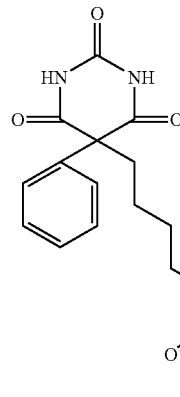

wherein R is aminodextran.

BRIEF DESCRIPTION OF THE DRAWINGS

The following detailed description of the embodiments of the present invention can be best understood when read in conjunction with the following drawings, where specific compounds are indicated with boldface reference numerals and in which.

DETAILED DESCRIPTION OF THE INVENTION

Figure 1:
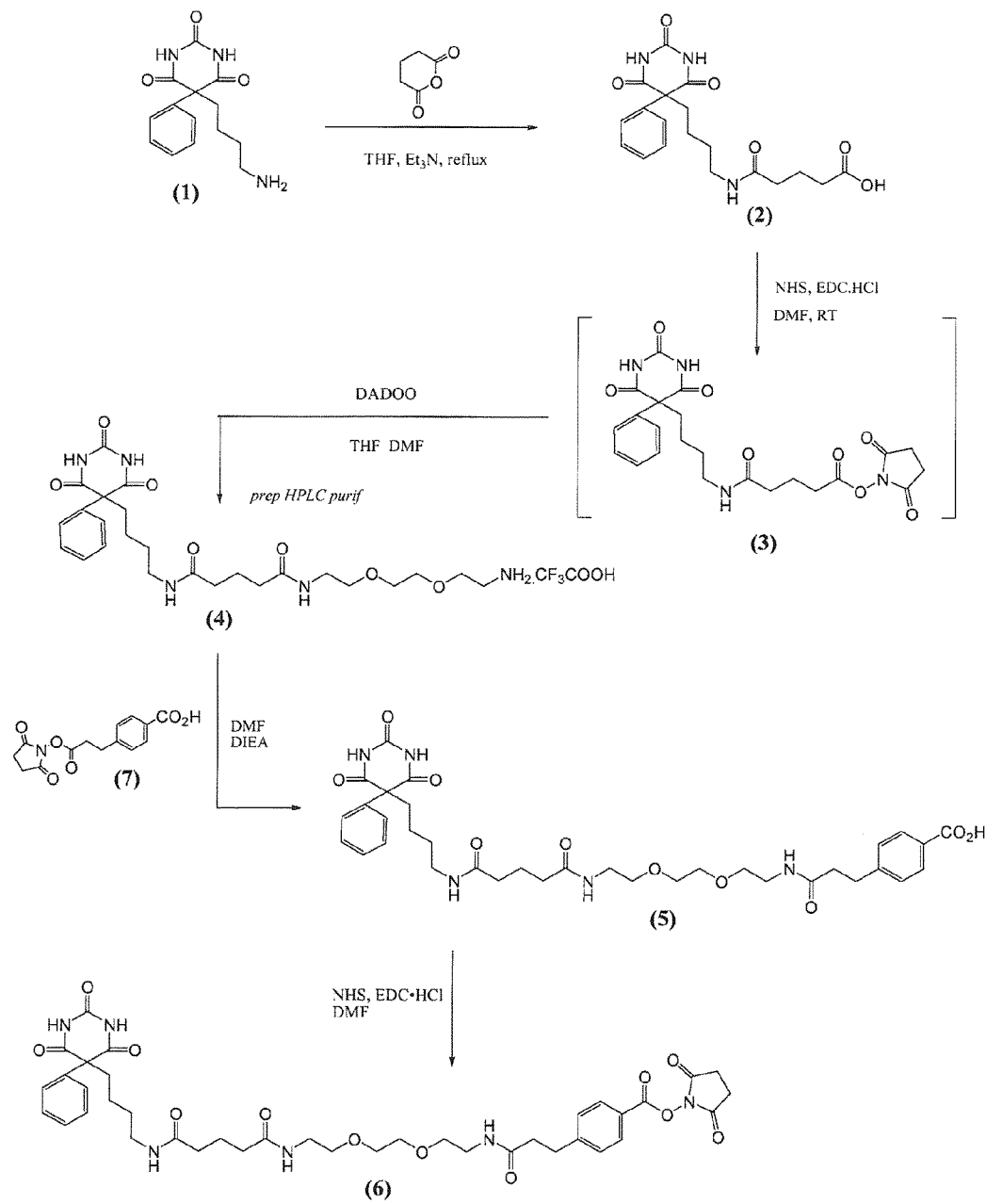
FIG. 1 shows the synthesis of 4-(2-{2-[2-(2-{4-[4-(2,4,6-trioxo-5-phenyl-hexahydro-pyrimidin-5-yl)-butylcarbamoyl]-butyrylamino}-ethoxy)-ethoxy]-ethylcarbamoyl}-ethyl)-benzoic acid 2,5-dioxo-pyrrolidin-1-yl ester, compound (6).
Figure 2:
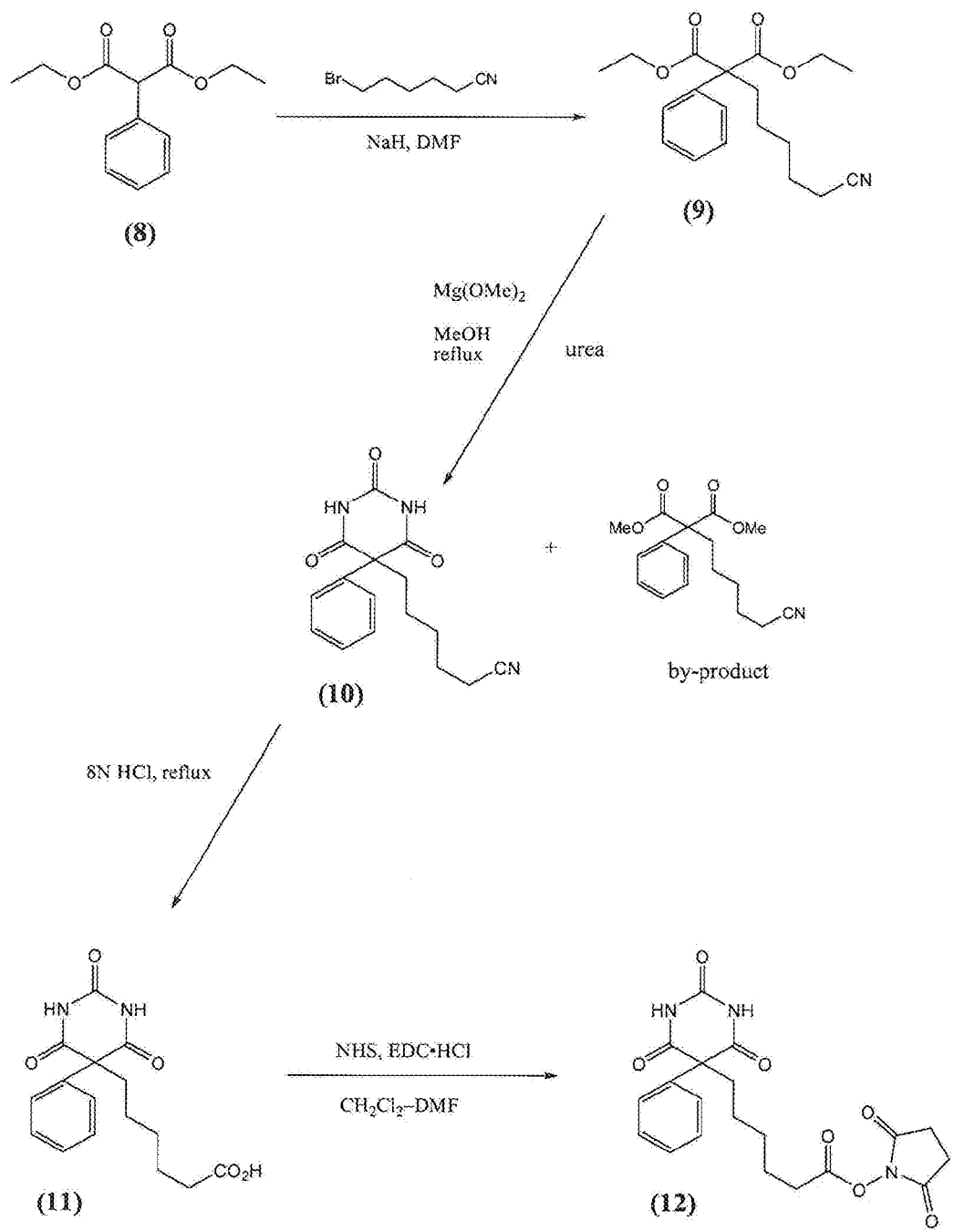
FIG. 2 shows the synthesis of 6-(2,4,6-trioxo-5-phenyl-hexahydro-pyrimidin-5-yl)-hexanoic acid 2,5-dioxo-pyrrolidin-1-yl ester, compound (12).
Figure 3:
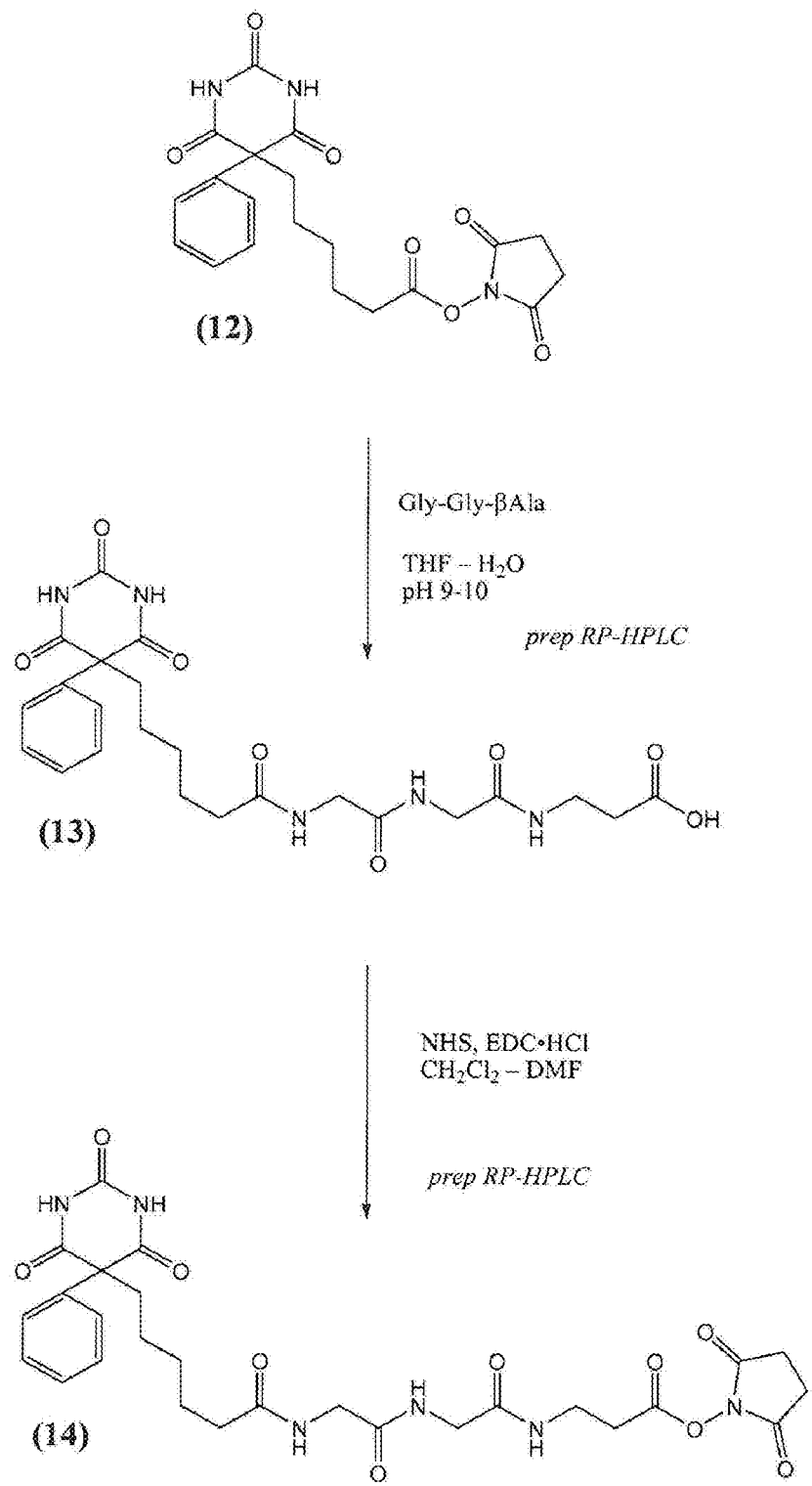
FIG. 3 shows the synthesis of 3-(2-{2-[6-(2,4,6-trioxo-5-phenyl-hexahydro-pyrimidin-5-yl)-hexanoylamino]-acetylamino}-acetylamino)-propionic acid 2,5-dioxo-pyrrolidin-1-yl ester, compound (14).
Figure 4:
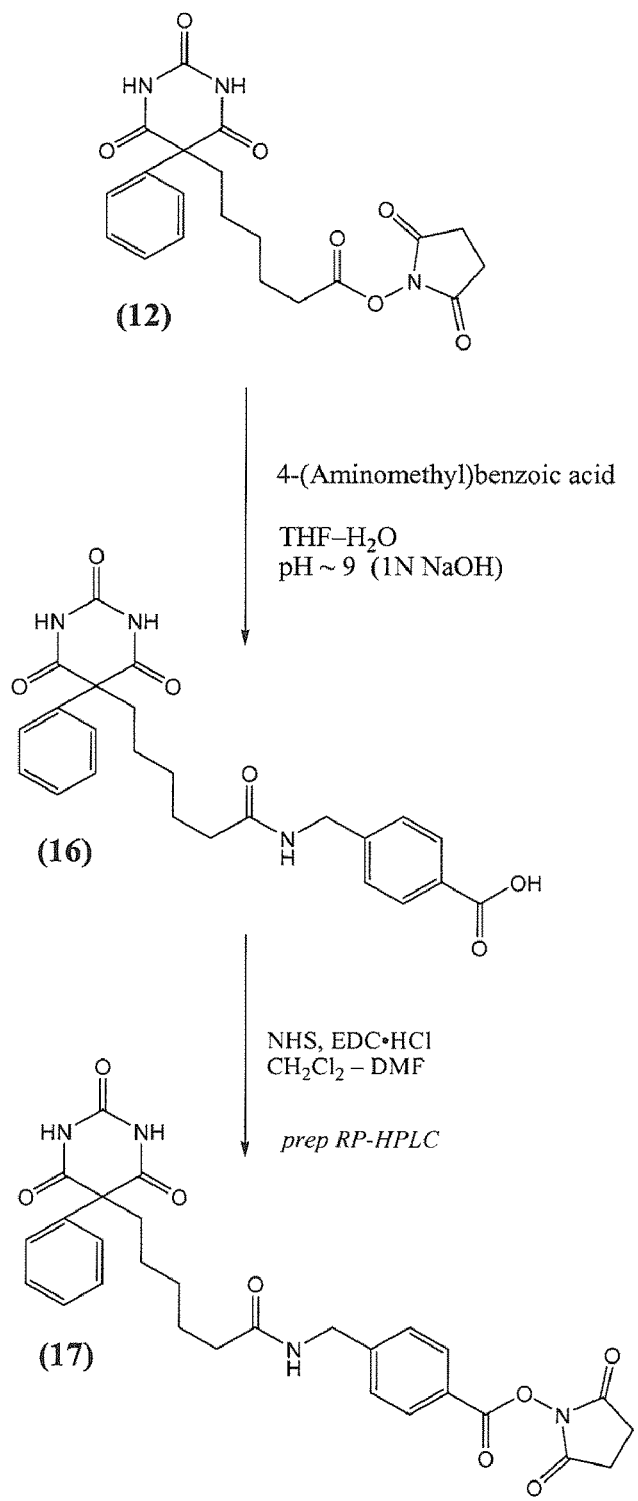
FIG. 4 shows the synthesis of 4-{[6-(2,4,6-trioxo-5-phenyl-hexahydro-pyrimidin-5-yl)-hexanoylamino]-methyl}-benzoic acid 2,5-dioxo-pyrrolidin-1-yl ester, compound (17).
Figure 5:
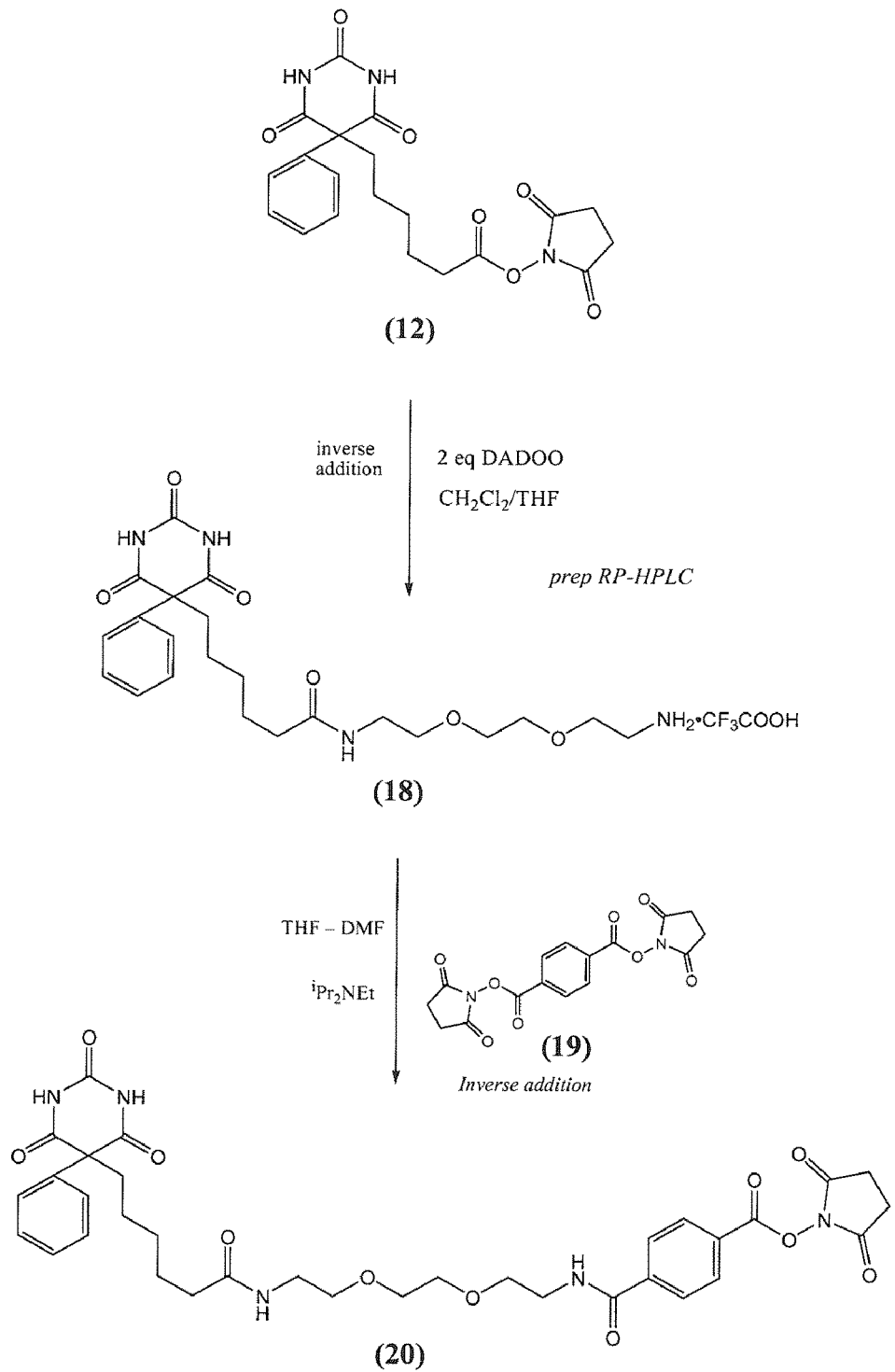
FIG. 5 shows the synthesis of N-[2-(2-{2-[6-(2,4,6-trioxo-5-phenyl-hexahydro-pyrimidin-5-yl)-hexanoylamino]-ethoxy}-ethoxy)-ethyl]-terephthalamic acid 2,5-dioxo-pyrrolidin-1-yl ester, compound (20).
Figure 6:
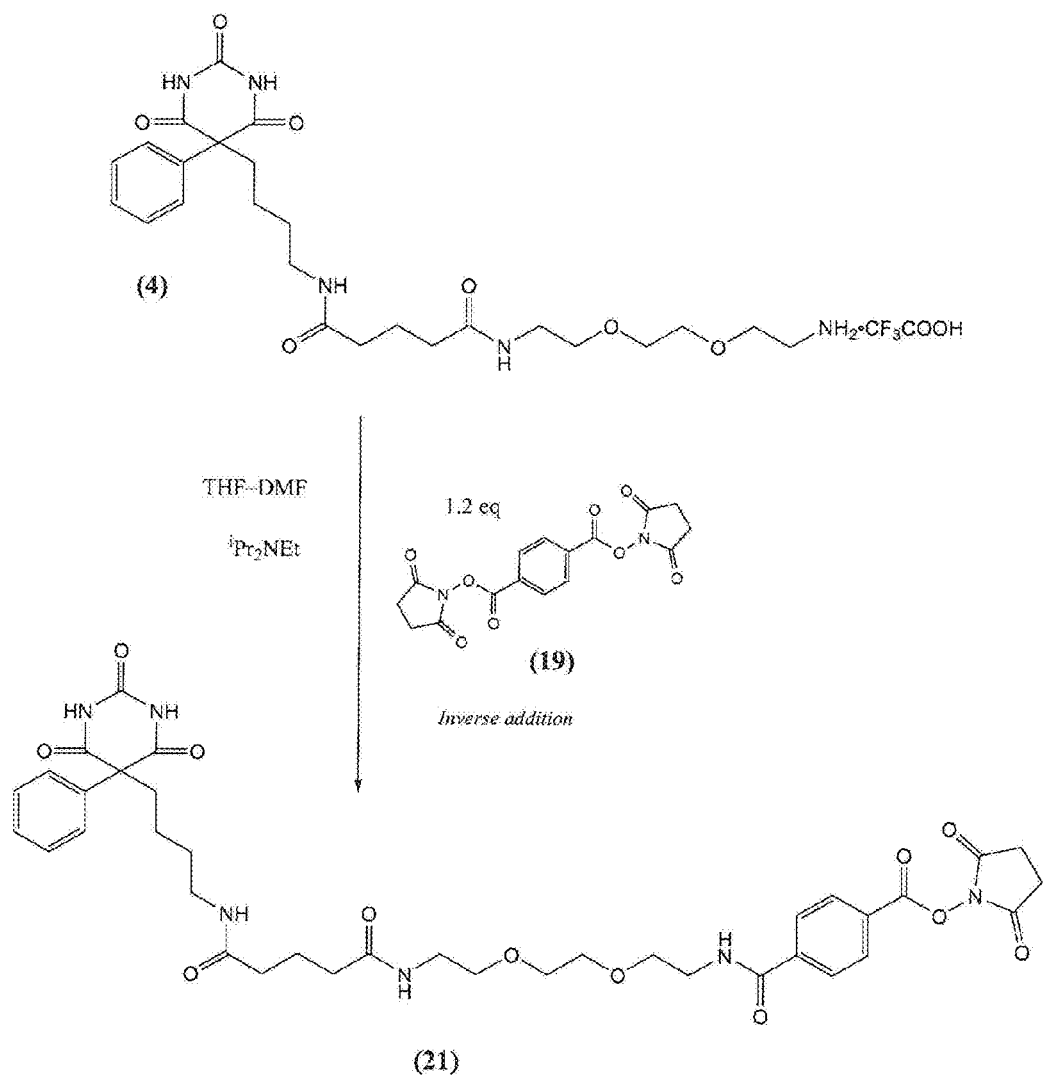
FIG. 6 shows the synthesis of N-{2-[2-(2-{4-[4-(2,4,6-trioxo-5-phenyl-hexahydro-pyrimidin-5-yl)-butylcarbamoyl]-butyrylamino}-ethoxy)-ethoxy]-ethyl}-terephthalamic acid 2,5-dioxo-pyrrolidin-1-yl ester, compound (21).

In the examples that follow, boldface numbers refer to the corresponding structure in the drawings.

Certain compounds of the present invention have the structure of Formula A:

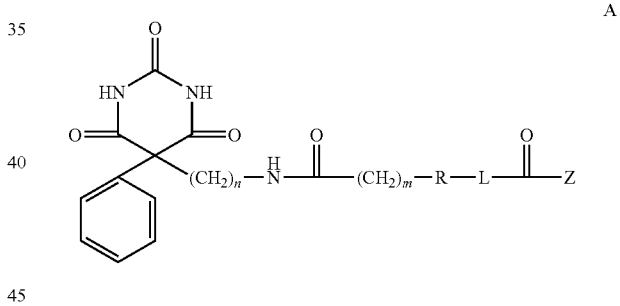

A wherein n is 4-6, m is 1-4, R is —NHCO— or —CONH—, L is a linking group comprising 2-18 carbon atoms and 1-6 heteroatoms arranged in a straight or branched chain and containing up to 1 cyclic structure, provided that the first atom attached to R is carbon, and Z is a leaving group or a polysaccharide.

Other compounds of the present invention have the structure of Formula B:

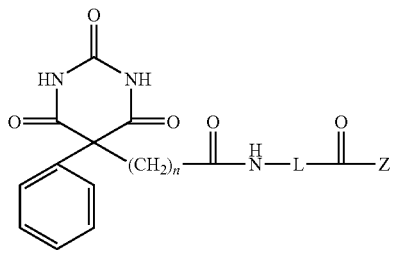

B wherein n is 4-6, L is a linking group comprising 2-18 carbon atoms and 1-6 heteroatoms arranged in a straight or branched chain and containing up to 1 cyclic structure, provided that the first atom attached to —CONH— is carbon, and Z is a leaving group or a polysaccharide There are known compounds with the core nucleus plus the (C2-C6)NH moiety out of the 5-position, as well as known compounds with the core nucleus plus the (C2 or C4)CO moiety out of the 5-position.

Figure 7:
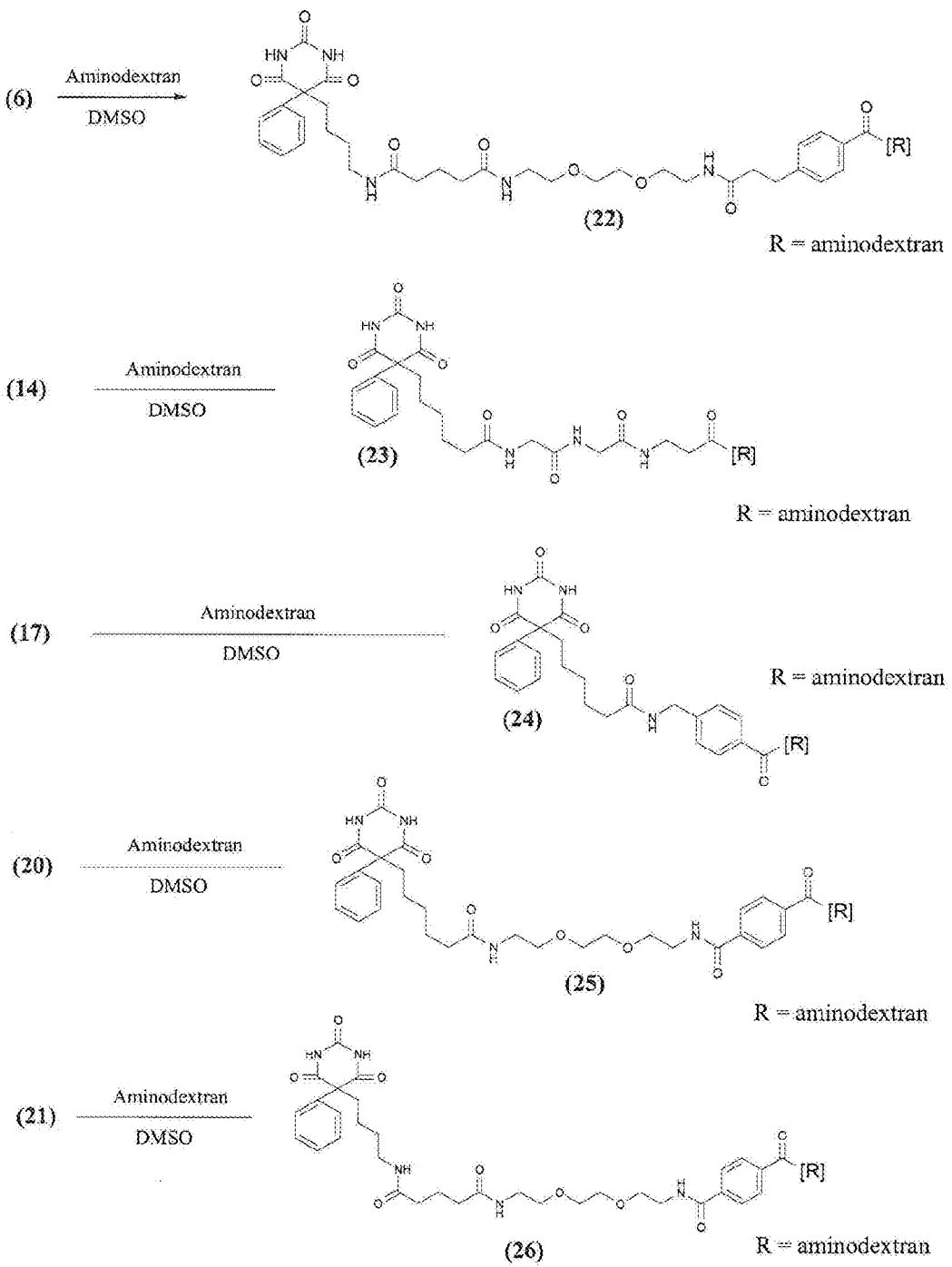
FIG. 7 shows the syntheses of aminodextran conjugates (22), (23), (24), (25), and (26) from the corresponding NHS esters (6), (14), (17), (20), and (21), respectively.

However, none of them carry an activated group at the end nor the arrangement of groups in compounds of the present invention, especially preferred compounds 6 and 21 of Formula A and additionally compound 14 of Formula B, which features hydrophilic linkers. These compounds were used to make the corresponding preferred aminodextran conjugates 22 and 26 as well as conjugate 23 (FIG. 7), of which 22 is especially preferred. Compounds 22-26 all gave very similar standard curves in the Roche ONLINE TDM assay format, but the substances of general Formula A in general turned out to have less false positive bias for negative samples over those of general Formula B, in particular over substance 20/25, which would be expected to have very similar gross physical properties to 14/23 but which was least preferred due to the distinct bias in the negative sample and which constituted an unexpected finding. Additionally, when considering substances of both general formulae as a whole, substance 20/25 would also be expected to have very similar gross physical properties to substance 21/26 where both have the DADOO-phthalate part-structure predominating in the overall linking chain, yet substance 20/25 (the least preferred) had appreciably greater bias in the negative sample compared with substance 21/26 (second most preferred). This too comprised part of the unexpected finding.

6

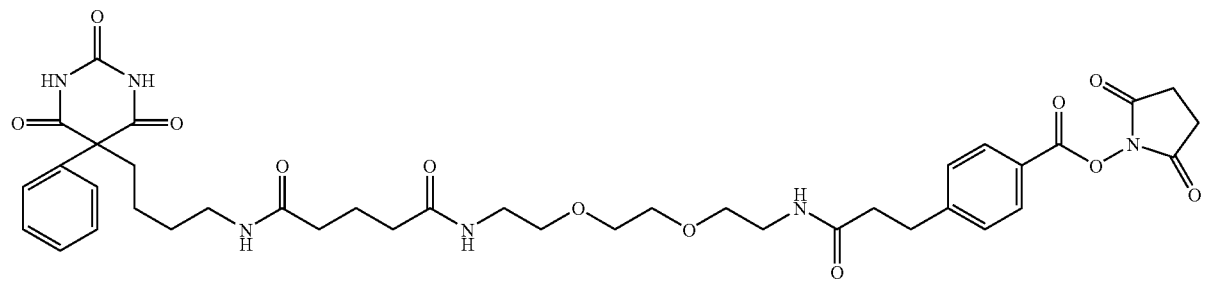

14

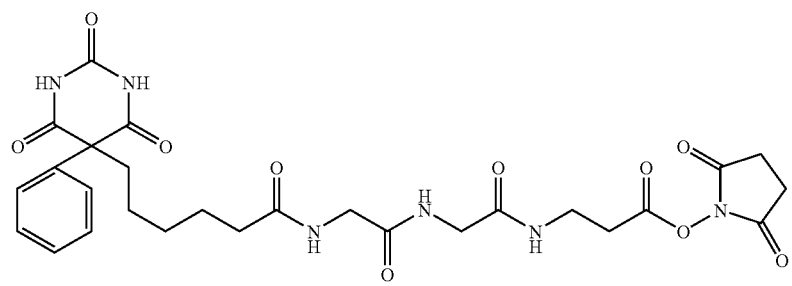

17

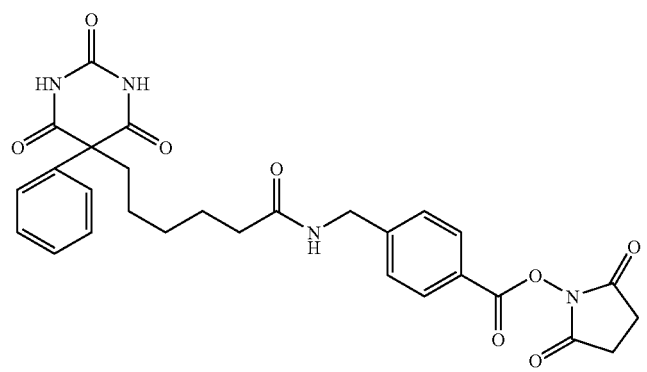

20

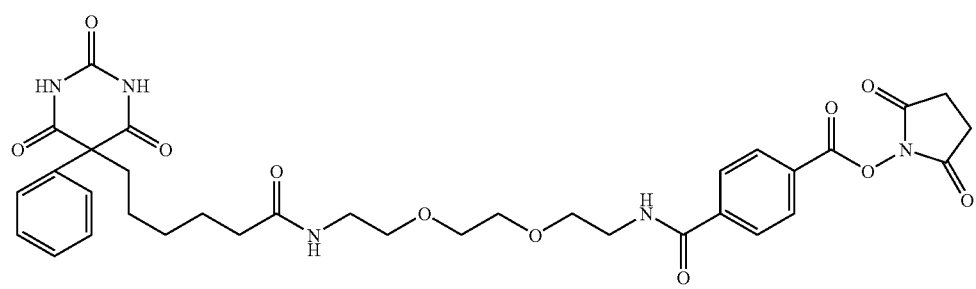

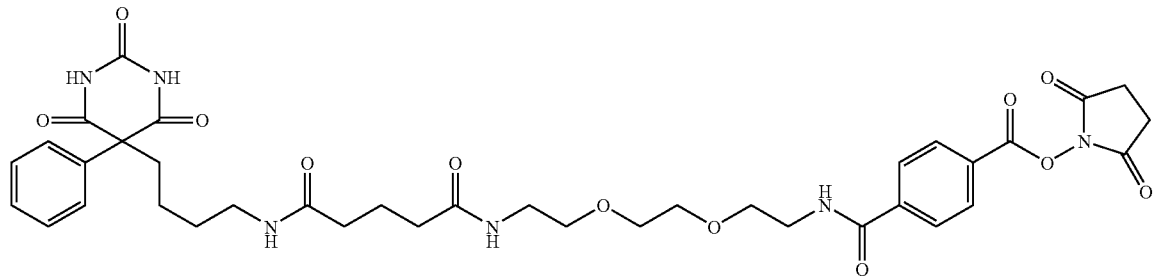

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Figure 8:
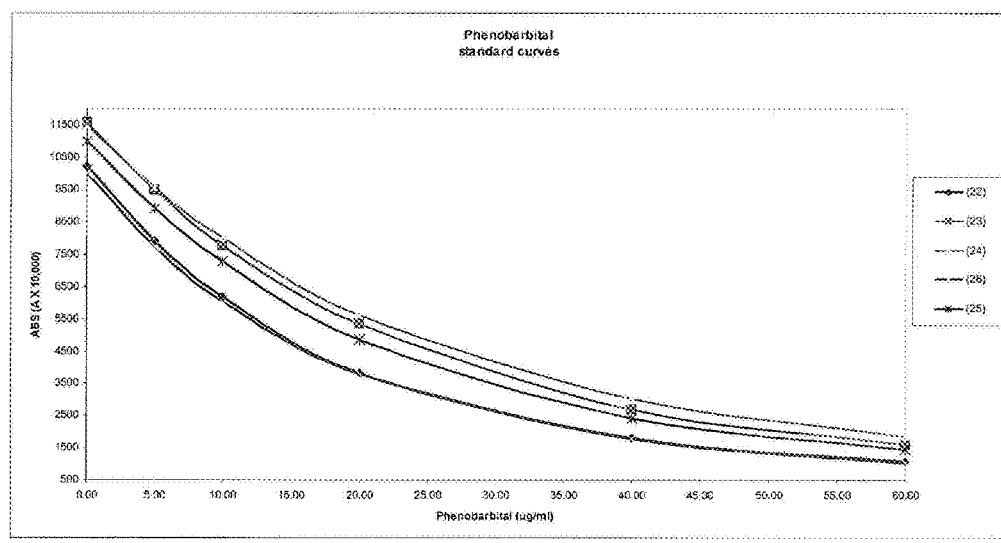
FIG. 8 shows the standard curves generated by using the aminodextran conjugates (22), (23), (24), (25), and (26) according to Example 21.

The synthetic schemes shown in FIGS. 1 through 7 show the syntheses of the five labels assessed for use in the Roche ONLINE TDM immunoassay for phenobarbital. The preferred labels were compounds 6, 14, and 21, with the preferred aminodextran conjugates being the corresponding compounds 22, 23, and 26. FIG. 8 shows the standard curves generated on a Roche-Hitachi 917 instrument (Roche Diagnostics GmbH) using all five aminodextran conjugates (see FIG. 7) showing the closeness of fit between each other. The table in Example 22 shows the apparent concentration of phenobarbital found in negative serum samples (i.e., containing no actual phenobarbital) using each of the different aminodextran conjugates and reading off the respective standard curve.

Aminodextran conjugates are formed from the phenobarbital derivatives of the present invention and contain multiple drug moieties per aminodextran molecule. These conjugates, dissolved in buffer, bind to antibodies specific for phenobarbital immobilized onto microparticles suspended in a buffer in the KIMS microparticle agglutination assay format. The aminodextran conjugates bridge across microparticles, and agglutination of the microparticles occurs at a certain rate. The rate of agglutination is measured by changes in light transmission of the sample. Free phenobarbital competes with binding of the conjugate to antibodies on the microparticles, and agglutination is inhibited (rate of agglutination falls) in a dose-response manner, which diminishes the rate of increasing absorbance of the sample in proportion to the concentration of free phenobarbital. Plots of the kinetic rate differences are then used to measure phenobarbital levels in serum samples. Use of the most preferred conjugate 22 resulted in an assay with the least bias in negative samples.

An earlier immunoassay in a microparticle format (U.S. Pat. No. 5,618,926) is directed toward the detection of barbiturates as a class, not specific for phenobarbital, with phenobarbital having a 29% cross-reactivity. The format is one in which the derivative is a secobarbital derivative conjugated to BSA and immobilized on the microparticle, with antibody in solution.

The prior art has synthesized derivatives out of the 5-position of the phenobarbital nucleus but without the specific linkers or activated groups at the end which are in general features of the present invention. In particular, it has not been taught that use of hydrophilic linkers confers an advantage, nor that there were unusual differences between slight variations between such hydrophilic linkers. E.g., it was discovered by the present inventors that subtle differences, in particular between the —NHCO—$(CH_2)_m$—R-L-CO—Z and —CONH-L-CO—Z substructures could result in an undesirable bias in negative samples.

Another aspect of the present invention relates to kits useful for conveniently performing assay methods using conjugates of the invention for the determination of phenobarbital. To enhance the versatility of the subject invention, reagents useful in the methods of the invention can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the components.

The kit of the present invention comprises an antibody specific for phenobarbital, a conjugate according to the invention, e.g., aminodextran conjugate (22), (23), (24), (25), or (26), and optional ancillary reagents. The reagents may remain in liquid form or may be lyophilized. For performing a microparticle agglutination assay according to present invention, the antibody is conjugated to a microparticle. The kit can further comprise, in packaged combination, a set of instructions or directions for use in performing the assay and calibration and control materials.

The assay of the invention is based on the kinetic interaction of microparticles in a solution (KIMS). Phenobarbital antibody is covalently coupled to microparticles, and the drug derivative is linked to a macromolecule, e.g., aminodextran. The kinetic interaction of microparticles in solutions is induced by binding of drug-conjugate to the antibody on the microparticles and is inhibited by the presence of phenobarbital in the sample. A competitive reaction takes place between the drug conjugate and phenobarbital in the serum sample for binding to the phenobarbital antibody on the microparticles. The resulting kinetic interaction of microparticles is indirectly proportional to the amount of drug present in the sample.

In order that the invention may be more readily understood, reference is made to the following examples, which are intended to illustrate the invention but not limit the scope thereof.

SPECIFIC EMBODIMENTS

In the examples that follow, boldface numbers refer to the corresponding structure in the drawings.

Reagents were obtained from Aldrich Chemical Company unless otherwise stated. All solvents were obtained from J. T. Baker and were of A.C.S. grade or HPLC grade or better unless otherwise stated. Triethylamine was obtained from Fluka Chemical Co. (Cat#90340; puriss.; ≧99.5%) Diisopropylethylamine (DIEA), dry dimethylsulfoxide (DMSO) and dry dimethylformamide (DMF) were obtained from Aldrich Chemical Co. All additions/withdrawals and manipulation of anhydrous solvents were performed by syringe/needle. Tetrahydrofuran (THF) was dried by boiling over and distillation from sodium/benzophenone under argon. Methylene chloride was dried by boiling over and distillation from calcium hydride under argon. Column chromatography was performed using flash-grade silica gel from E.M. Science (Cat. #9385-9; Silica gel 60; 230-400 mesh ASTM) and under a positive pressure of nitrogen. Thin layer chromatography (TLC) was performed using silica gel plates obtained from E.M. Science (Cat. #5715-7; 0.025 cm thickness) Mixed solvents are expressed as volume for volume percentages. (e.g., 10% MeOH—CHCl$_3$ is chloroform containing 10% of methanol by volume) HPLC analyses were performed on an Agilent 1100 LC/MS system; configured with a diode-array detector and a quaternary pump. The LC analyses were performed with a Vydac 218TP54 column (RP-C18; 300 Å, 5µ) equipped with a Phenomenex guard module (Phenomenex KJO-4282/C18 ODS 5µ), with the chromatographic stream ported post-column into the MS detector. The MSD utilized was run in ES (+) mode (electrospray; positive mode. Preparative RP-HPLC was performed on a Varian Dynamax (Rainin) system employing two SDI titanium head 2000 psi pumps with a Varian Dynamax UV-C variable wavelength detector. Separations were carried out on modular Varian Dynamax radial compression columns—either: Column I (R00083221C; Microsorb 60-8, C18, 250×21.4 mm) equipped with a guard module (R00083221G; C18, 8µ); or: Column II (R00083241C; Microsorb 60-8, C18, 250×41.4 mm) equipped with a guard module (R00083241G; C18, 8µ) $^1$H-NMR spectra were obtained at 200 MHz on a Varian Gemini 2000, or at 400 MHz on a Varian XL-400 spectrometer, each equipped with a Sun/Sparc station.

Example 1

Synthesis of Compound (1)

To a stirring solution of 101 mg (0.259 mmol) of compound (1) [a) Krausz, L. M.; Hitz, J. B.; Buckler, R. T. and Burd, J. F. Therapeutic Drug Monitoring, 1980, 2, 261-272; b) Castro, A.; Chung, A. and Monji, N. Research Communications in Chemical Pathology and Pharmacology, 1980, 28, 309-317.] in 15 mL of dry THF at RT containing 76 µL (0.55 mmol; 2.1 eq) of triethylamine was added 47 mg (0.41 mmol; 1.6 eq) of glutaric anhydride. After stirring briefly at RT the reaction was boiled under reflux (oil bath at 90° C.) under argon. Analysis by RP-HPLC after 1 hr indicated the reaction was complete, with a single main product peak. The reaction was evaporated to dryness (rotovap) under reduced pressure. The residue was redissolved in ~2.5 mL of 1:1 MeCN/water, filtered (0.45µ) and purified by preparative RP-HPLC [Column I], eluting with a gradient of 5% (0 min)→100% (20 min)→100% (22 min)→5% (27 min) of 0.1% TFA/MeCN in 0.1% TFA/water; 20 mL/min. Fractions containing product were combined, MeCN removed under reduced pressure, the aqueous residue frozen (dry-ice/acetone) and lyophilized overnight to give compound (2) as a white powdery solid. (99 mg, 98% yield) LC/MS: $t_R$~8.8 min [5% (0 min)→88% (17.5 min) of 0.1% TFA/MeCN in 0.1% TFA/water]; Observed M+H 390.1. $^1$H-NMR: compatible.

Example 2

Synthesis of Compound (3)

To a stirring solution of 54.1 mg (0.139 mmol) of compound (2) in 4 mL of dry DMF under argon was added 16.1 mg (0.140 mmol) of N-hydroxysuccinimide (NHS) and 38.1 mg (0.199 mmol) of 3-ethyl-1-dimethylaminopropylcarbodiimide hydrochloride (EDC.HCl) and the solution stirred at RT under argon for ~3 h. LC/MS indicated partial formation of the NHS ester. A further 32.3 mg (0.281 mmol; total added=0.421 mmol, 3 eq) of NHS and 55.3 mg (0.288 mmol; total added=0.487 mmol, 3.5 eq) of EDC.HCl were added and the reaction stirred overnight at RT under argon. LC/MS indicated essentially complete conversion to the desired NHS ester (3). LC/MS: $t_R$~10.0 min [5% (0 min)→88% (17.5 min) of 0.1% TFA/MeCN in 0.1% TFA/water]; Observed M+H 487.1. The entire product mixture/solution was used as-is in the next step [see Example 3] without further purification.

Example 3

Synthesis of Compound (4)

To a solution of 81.2 µL (~0.554 mmol; ~4 eq) [by pipette] of 2,2'-(ethylenedioxy)-diethylamine [Fluka 03739](DA-DOO) in 4 mL of dry THF and 2 mL of dry DMF at RT under argon was added the entire reaction/product mixture (~4 mL) containing (3) (from Example 2; transferred by syringe to a small addition funnel) dropwise over 20 min. while maintaining efficient stirring. The flask from Example 2 and addition funnel were washed down with 4 mL of dry THF and the washings added dropwise to the reaction over ~15 min. Analysis of the reaction after ~0.5 h showed disappearance of the NHS ester (3) and formation of the desired product (4) ($t_R$~8.25 min) with a small amount of a dimeric substance. The reaction was evaporated under reduced pressure to remove THF, then under high vacuum (high vac rotovap) to remove DMF. The residue was re-dissolved in 1:1 MeCN/water, filtered (0.45µ) and purified by preparative RP-HPLC, eluting with a gradient of 5% (0 min)→100% (20 min)→100% (22 min)→5% (27 min) of 0.1% TFA/MeCN in 0.1% TFA/water; 40 mL/min. The product fraction was evaporated under reduced pressure to remove MeCN, the aqueous residue frozen (dry-ice/acetone) and lyophilized overnight to give compound (4) (assigned as the mono-TFA salt) as a white solid. (55 mg, 60% yield over two steps) LC/MS: $t_R$~8.26 min [5% (0 min)→88% (17.5 min) of 0.1% TFA/MeCN in 0.1% TFA/water]; Observed M+H 520.2, M+Na 542.2. $^1$H-NMR: compatible.

Example 4

Synthesis of Compound (5)

To a solution of 49.7 mg (0.078 mmol) of compound (5) and 23.9 mg (0.082 mmol, 1.05 eq) of compound (7) [see Example 6] in 2 mL of dry DMF at RT under argon was added 43.8 µL of diisopropylethylamine (DIEA) and the clear solution stirred rapidly. Analysis by LC/MS after ~3 h indicated formation of product plus a small amount of a by-product eluting after product, plus residual starting material. A further 5.0 mg (0.017 mmol; total added=0.099 mmol, 1.27 eq) of (7) was added and stirring continued at RT. Analysis after 1 h by LC/MS indicated a trace of starting material remaining. The reaction was evaporated under high vacuum (high vac rotovap). The residue was redissolved in 1:1 MeCN/water, filtered (0.45µ) and purified by preparative RP-HPLC, eluting with 15% (0 min)→60% (20 min)→100% (22 min)→15% (27 min) of 0.1% TFA/MeCN in 0.1% TFA/water; 20 mL/min. The product fractions were pooled, MeCN evaporated off under reduced pressure, the aqueous residue frozen (dry-ice/acetone) and lyophilized overnight to give compound (5) as a white solid. (29.7 mg, 55% yield) LC/MS: $t_R$~10.1 min [15% (0 min)→60% (20 min)→100% (25 min)→15% (30 min) of 0.1% TFA/MeCN in 0.1% TFA/water]; Observed M+H 696.2, M+Na 718.2. $^1$H-NMR: compatible.

Example 5

Synthesis of Compound (6)

To a stirring solution of 20.4 mg (0.029 mmol) of compound (5) in 3 mL of dry DMF at RT under argon was added 6.4 mg (0.056 mmol, 1:9 eq) of NHS and 10.5 mg (0.055 mmol, 1.9 eq) of EDC.HCl followed by 11.5 µL of triethylamine and the reaction stirred at RT overnight. Analysis by LC/MS indicated incomplete reaction. A further 12.8 mg (0.111 mmol, 3.8 eq) of NHS and 20.7 mg (0.108 mmol, 3.7 eq) of EDC.HCl were added and stirring continued at RT overnight. Re-analysis by LC/MS now indicated the reaction was complete. The reaction was evaporated to dryness (high vac rotovap) and the residue directly purified by silica gel column chromatography [~10 mm length×~1½ mm I.D. column], prepacked and eluted with 10% MeOH in $CH_2Cl_2$. Fractions containing product were combined, evaporated under reduced pressure, swirled with dry $CH_2Cl_2$ and re-evaporated, repeating the process several times. The residue was dried under high vacuum to give compound (6) as a white solid. (18.1 mg, 79% yield). LC/MS: $t_R$~10.55 min [5% (0 min)→88% (17.5 min) of 0.1% TFA/MeCN in 0.1% TFA/water]; Observed M+H 793.2, M+Na 815.2. $^1$H-NMR: compatible.

Example 6

Synthesis of Compound (7)

A stirring suspension of 3-(4-carboxyphenyl)propionic acid (Lancaster Chemical Company) and 1 eq. N-hydroxysuccinimide (Aldrich Chemical Company) in dry THF at RT was treated and reacted with 1 eq of t-butyl isocyanide (Aldrich Chemical Company) for several days, followed by simple filtration of the product, compound (7) (fine solids), washing with THF and drying under vacuum.

Example 7

Synthesis of Compound (21)

To a vigorously stirring solution of 17.9 mg (0.05 mmol) of compound (19) [see Example 52 in U.S. Pat. No. 6,811,998] in 1 mL of dry DMF and 4 mL of dry THF at RT was added dropwise (by addition funnel) a solution of 26.0 mg (0.04 mmol) of compound (4) in 2 mL of dry DMF and 5 mL of dry THF containing 22 µL of diisopropylethylamine (DIEA). Analysis by LC/MS after about 2 h indicated essentially complete reaction with formation of product (21). Solvent was stripped from the reaction (rotovap, then high vacuum rotovap) and the residue purified by silica gel column chromatography [prepacked in acetonitrile (MeCN)-THF (7:3); eluted with MeCN-THF (7:3) then with MeCN-THF (3:7). Fractions containing product were collected, combined and evaporated. The residue was redissolved/swirled with dry $CH_2Cl_2$ and re-evaporated (repeated once) then dried under high vacuum overnight to give slightly impure compound (21). The material was re-dissolved in 1:1 MeCN/water, filtered (0.45 g) and repurified by preparative RP-HPLC, eluting with a gradient of 15% (0 min)→100% (20 min)→100% (23 min)→15% (28 min) of 0.1% TFA/MeCN in 0.1% TFA/water; 20 mL/min. The product fraction was immediately frozen (dry-ice/acetone), MeCN sublimated off (high vacuum rotovap, dry-ice/acetone condenser insert) and the still frozen residue lyophilized overnight to give compound (21). (9.8 mg, ~30% overall) LC/MS: $t_R$~9.64 min [15% (0 min)→100% (20 min) of 0.1% TFA/MeCN in 0.1% TFA/water]; Observed M+H 765.2, M+Na 787.2. $^1$H-NMR: compatible.

Example 8

Synthesis of Compound (9)

2.54 g of a 60% dispersion of sodium hydride in mineral oil (equiv. to 1.524 g actual substance, 0.0635 mol) (Aldrich Chemical Company) in a round-bottom flask equipped with a stir bar was washed with dry hexanes (3×10 mL), pipetting off the hexanes each time. The washed sodium hydride was briefly dried under vacuum, then suspended in 30 mL of dry DMF under argon. To the stirring suspension was added 9.12 mL (10.0 g, 0.0423 mol) of diethyl 2-phenylmalonate (Aldrich Chemical Company) by syringe over about 15 m, moderating the exothermic reaction with a water bath as needed, and the reaction stirred for 10 m. To the resulting mixture was added 8.42 mL (11.18 g, 0.0635 mol) of 6-bromohexanenitrile (Aldrich Chemical Company) dropwise by syringe over about 5 m and the brown-colored reaction stirred overnight. Analysis by LC/MS indicated formation of product (9). The reaction was quenched with 200 mL of 100 mM potassium phosphate pH 7 and extracted with $CH_2Cl_2$. The pH of the aqueous layer was readjusted to about 7 with dil. HCl and re-extracted with $CH_2Cl_2$ (×2). The combined organic phases were washed with 100 mM potassium phosphate pH 7, then with sat. aq. NaCl, dried ($Na_2SO_4$) and evaporated to give a viscous oil. Purification by silica gel column chromatography (prepacked in 20% EtOAc-hexanes, eluting with same) then gave the product (9), in two cuts of fraction groups, as a viscous liquid. (combined yield 8.28 g, 59%) LC/MS: $t_R$~16.28 min [5% (0 min)→88% (17.5 min) of 0.1% TFA/MeCN in 0.1% TFA/water]; Observed M+H 332.2, M+Na 354.2. $^1$H-NMR: compatible.

Example 9

Synthesis of Compound (10)

A solution of magnesium methoxide was prepared by dissolution of 440 mg (18.1 mmol) of magnesium turnings (Aldrich Chemical Company) in 10 mL of anhydrous methanol with careful heating (initiation of reaction) and careful boiling for 1 h under argon. To this solution was added 905 mg (15.09 mmol) of urea (Aldrich Chemical Company), pre-dried at 70° C., and boiling continued for about 15 m. The reaction was cooled slightly and to the warm solution was added 2.0 g (6.035 mmol) of compound (9). The reaction was boiled for about 20 h, following by LC/MS, then cooled to RT. Methanol was removed (rotovap) from the heterogeneous mixture, the residue treated with water, the mixture acidified with 6N HCl to pH about 3 to 4, and the mixture extracted twice with EtOAc. The combined organic phases were washed with two-thirds sat. NaCl, sat. NaCl, dried ($Na_2SO_4$), evaporated (rotovap) and dried under high vacuum to give crude product as a semi-crystalline gum. This was triturated with about 10 mL of 50% EtOAc-hexanes. The resulting solids were filtered off, washing with a little 50% EtOAc-hexanes, and dried to give a first crop of 639 mg of compound (10). The mother liquors were concentrated to dryness and the residue triturated with 50% EtOAc-hexanes. The resulting solids were filtered off, washing with a little 50% EtOAc-hexanes, and dried to give 99 mg of compound (10) in a second crop. Combined yield: 738 mg, 41%. LC/MS: $t_R$~10.93 min [5% (0 min)→100% (20 min) of 0.1% TFA/MeCN in 0.1% TFA/water]; Observed M+H 300.1, M+Na 322.1. $^1$H-NMR: compatible.

Example 10

Synthesis of Compound (11)

A stirring suspension of 408 mg (1.363 mmol) of compound (10) in 6 mL of 8N HCl was boiled overnight (oil bath at 120° C.) under argon and under a reflux condenser. The reaction was cooled to RT. The white solids were filtered off, washed thoroughly with water, air dried with vacuum assist then dried under high vacuum to give compound (11) as a white solid of good purity. (376 mg, 87%) LC/MS: t 9.94 min [5% (0 min)→100% (20 min) of 0.1% TFA/MeCN in 0.1% TFA/water]; Observed M−OH 301.1, M+H 319.1, M+Na 354.2. $^1$H-NMR: compatible.

Example 11

Synthesis of Compound (12)

To a semi-solution of 200 mg (0.63 mmol) of compound (11) and 80 mg (0.695 mmol) of N-hydroxysuccinimide (Aldrich Chemical Company) in 10 ml., of dry $CH_2Cl_2$ was added 133 mg (0.695 mmol) of EDC.HCl (Sigma Chemical Company) followed by 0.5 mL of dry DMF to aid in dissolution of the substances. After stirring overnight at RT under argon, LC/MS analysis of the clear solution indicated the reaction was essentially complete. The reaction was diluted with $CH_2Cl_2$ (excess) and the organic phase washed sequentially with 0.1N HCl diluted with sat. NaCl, half-saturated NaCl, sat. NaCl; dried ($Na_2SO_4$) and evaporated (rotovap) to give 329 mg of the NHS ester product (12) in acceptable purity. LC/MS: $t_R$~11.43 min [5% (0 nm in)-100% (20 min) of 0.1% TFA/MeCN in 0.1% TFA/water]; Observed M+H 416.1, M+Na 438.1. $^1$H-NMR: compatible, plus DMF and traces impurities (byproduct [N-(dimethylaminopropyl)-N'-ethylurea] of the activation reaction). The material was used without further purification.

Example 12

Synthesis of Compound (13)

To a stirring solution of 159 mg of crude compound (12) [from Example 11] in 5 mL of dry THF under argon was added a solution of 100 mg (0.492 mmol) of glycyl-glycyl-β-alanine) (Gly-Gly-βAla) (Bachem Americas, Cat#H-3295) in a total of 5 mL of water. The reaction turned cloudy followed by appearance of fine solid precipitates. The pH was adjusted with dropwise addition of 1N NaOH to pH about 9 to 10 over about 20 m (reaction cleared up). LC/MS analysis indicated the reaction was complete. Solvent (THF) was evaporated off (rotovap) and the aqueous residue diluted with a little MeCN, filtered, re-diluted with a little MeCN and water to maintain a clear solution, and purified over several runs by preparative RP-HPLC, eluting with a gradient of 5% (0 min)→100% (20 min)→100% (22 min)→5% (27 min) of 0.1% TFA/MeCN in 0.1% TFA/water; 40 mL/min. The main product fractions were combined, evaporated under reduced pressure to remove MeCN, the aqueous residue frozen (dry-ice/acetone) and lyophilized overnight to give compound (13) as a white solid. (97 mg, 61% yield over two steps) LC/MS: $t_R$~8.37 min [5% (0 min)→88% (17.5 min) of 0.1% TFA/MeCN in 0.1% TFA/water]; Observed M+H 504.1, M+Na 526.1. $^1$H-NMR: compatible.

Example 13

Synthesis of Compound (14)

To a stirring semi-solution of 50 mg (0.099 mmol) of compound (13) and 13 mg (0.109 mmol) of N-hydroxysuccinimide (NHS) (Aldrich Chemical Company) in 5 mL of dry $CH_2Cl_2$ under argon was added 21 mg (0.109 mmol) of EDC.HCl (Sigma Chemical Company) followed by 1 mL of dry DMF. After stirring overnight at RT a further 27 mg of NHS and 30 mg of EDC.HCl were added and stirring continued for a second overnight period. LC/MS analysis indicated formation of product with small amounts of starting material and impurities. The reaction was diluted with EtOAc, washed with [0.1N HCl+sat. NaCl (1:1)], half-saturated NaCl, sat. NaCl, dried ($Na_2SO_4$) and evaporated (rotovap). The residue was re-dissolved in 1:1 MeCN/water, filtered (0.45µ) and purified by preparative RP-HPLC, eluting with a gradient of 5% (0 min)→100% (20 min)→100% (22 min)→5% (27 min) of 0.1% TFA/MeCN in 0.1% TFA/water; 40 mL/min. The product fraction was immediately frozen (dry-ice/acetone), MeCN sublimated off (high vacuum rotovap, dry-ice/acetone condenser insert) and the still frozen residue lyophilized overnight to give compound (14). (18 mg, ~31% overall) LC/MS: $t_R$~9.18 min [5% (0 min)→88% (17.5 min) of 0.1% TFA/MeCN in 0.1% TFA/water]; Observed M+H 601.2, M+Na 623.2. $^1$H-NMR: compatible.

Example 14

Synthesis of Compound (16)

To a stirring solution of 84 mg of crude compound (12) [see Example 11] in 4 mL of dry THF under argon was added 32 mg (0.212 mmol) of 4-(aminomethyl)benzoic acid (Aldrich Chemical Company) followed by 2 mL of water. The pH of the heterogeneous reaction mixture was adjusted to about 9 to 10 with 0.1N, then 1N NaOH, over about 15 m to give an almost clear reaction solution. After 0.5 h, LC/MS analysis indicated the reaction was complete. The pH was adjusted to about 4 to 5 with 1N HCl and solvent stripped off (rotovap, then high vacuum rotovap) and the residue dried under high vacuum. The material was re-dissolved in 1:1 MeCN/water, filtered (0.45μ) and purified by preparative RP-HPLC, eluting with a gradient of 5% (0 min)→100% (20 min)→100% (22 min)→5% (27 min) of 0.1% TFA/MeCN in 0.1% TFA/water; 20 mL/min. The product fractions were combined, most of the MeCN evaporated off (rotovap) and the aqueous residue frozen (dry-ice/acetone) and lyophilized overnight to give compound (16). (76 mg, 89% yield) LC/MS: $t_R$~10.37 min [5% (0 min)→88% (17.5 min) of 0.1% TFA/MeCN in 0.1% TFA/water]; Observed M+H 452.1, M+Na 474.2. $^1$H-NMR: compatible.

Example 15

Synthesis of Compound (17)

To a stirring semi-solution of 18 mg (0.04 mmol) of compound (16) and 23 mg (0.199 mmol) of N-hydroxysuccinimide (NHS) (Aldrich Chemical Company) in 4 mL of dry $CH_2Cl_2$ under argon was added 23 mg (0.12 mmol) of EDC.HCl (Sigma Chemical Company) and stirring continued overnight. The clear reaction was diluted with EtOAc and sequentially washed with 0.1N HCl diluted with sat. NaCl, half-saturated NaCl, sat. NaCl; dried ($Na_2SO_4$) and evaporated (rotovap). The resulting material was re-dissolved in 1:1 MeCN/water, filtered (0.45μ) and purified by preparative RP-HPLC, eluting with a gradient of 5% (0 min)→100% (20 min)→100% (22 min)→5% (27 min) of 0.1% TFA/MeCN in 0.1% TFA/water; 20 mL/min. The product fractions were combined, immediately frozen (dry-ice/acetone), MeCN sublimated off (high vacuum rotovap, dry-ice/acetone condenser insert) and the still frozen residue lyophilized overnight to give compound (17). (16 mg, 73%) LC/MS: $t_R$~11.48 min [5% (0 min)→88% (17.5 min) of 0.1% TFA/MeCN in 0.1% TFA/water]; Observed M+H 549.2, 2M+Na 1097.3. $^1$H-NMR: compatible.

Example 16

Synthesis of Compound (18)

A solution of a mixture of 100 mg (0.314 mmol) of acid compound (11), 40 mg (0.348 mmol) of NHS, and 65 mg (0.339 mmol) of EDC.HCl in 5 mL of dry THF and 5 mL of dry $CH_2Cl_2$ was stirred at RT under argon overnight. LC/MS analysis indicated fairly clean conversion to the NHS ester (12). All of this solution was transferred to a dropping funnel and added over about 15 m to a rapidly stirring solution of 93 mg (0.628 mmol) of 2,2'-(ethylenedioxy)-diethylamine [Fluka 03739](DADOO) in 10 mL of dry $CH_2Cl_2$. The initially clear reaction became hazy with fine oil droplets dispersed in the reaction mixture. LC/MS analysis of the reaction (aliquot of supernatant+oil) indicated the reaction was complete. Volatile material was evaporated off (rotovap), the residue redissolved in MeCN-water (1:1), acidified with trifluoroacetic acid (TFA) to pH about 3 to 4, filtered (0.45μ) and purified by RP-HPLC, eluting with a gradient of 5% (0 min) →100% (20 min)→100% (22 min)→5% (27 min) of 0.1% TFA/MeCN in 0.1% TFA/water; 40 mL/min. The main product fractions were combined, most of the MeCN evaporated off (rotovap) and the aqueous residue frozen (dry-ice/acetone) and lyophilized overnight to give compound (18) (120 mg, 68% yield), assigned as the TFA salt. LC/MS: $t_R$~8.49 min [5% (0 min)→88% (17.5 min) of 0.1% TFA/MeCN in 0.1% TFA/water]; Observed M+H 449.1. $^1$H-NMR: compatible.

A small amount of the "dimeric" compound (15) shown below was also isolated. (15.5 mg, 6.6%) LC/MS: $t_R$~11.07 min [5% (0 min)→88% (17.5 min) of 0.1% TFA/MeCN in 0.1% TFA/water]; Observed M+H 749.3, M+Na 771.3. $^1$H-NMR: compatible.

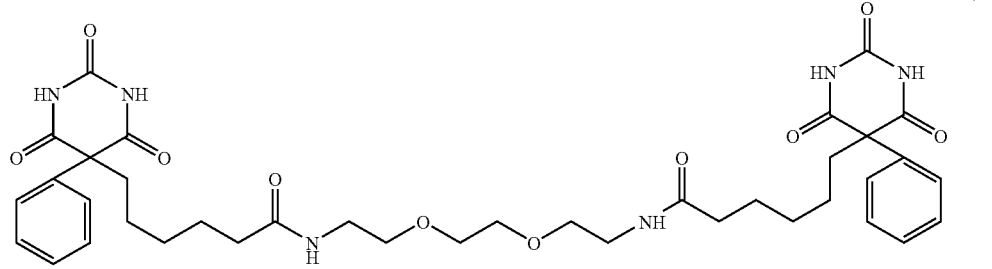

(15)

Example 17

Synthesis of Compound (20)

A solution of 102 mg (~0.181 mmol) of compound (18) in 5 mL of dry THF was added dropwise over about 10 m to a rapidly stirring solution of 98 mg (0.272 mmol) of the terephthalic diester compound (19) and 95 μL (~70 mg, ~0.543 mmol) of diisopropylethylamine in 5 mL of dry THF and 5 mL of dry DMF under argon. The dropping funnel was washed down with a little dry THF which was added to the reaction. LC/MS analysis after 0.5 h indicated the reaction was complete. The reaction was stripped to dryness (rotovap, then high vacuum rotovap) and dried under high vacuum. The residue was redissolved in 1:1 THF-MeCN, filtered from some insoluble material and the filtrate purified by silica gel column chromatography (prepacked in 1:1 THF-McCN, washed through with same before the product mixture was loaded, and eluting with same). Fractions containing product were combined, evaporated (rotovap), the residue taken up in dry $CH_2Cl_2$ and re-evaporated (rotovap) (repeated x2), dried under high vacuum, the resulting solids taken up again in dry $CH_2Cl_2$, re-evaporated then dried under high vacuum overnight to give compound (20) as a white foam/glass. (68 mg, 54%) LC/MS: $t_R$~10.87 min [5% (0 min)→88% (17.5 min) of 0.1% TFA/MeCN in 0.1% TFA/water]; Observed M+H 694.2, M+Na 716.2. $^1$H-NMR: compatible.

Example 18

Preparation of Aminodextran Conjugate (22)

To a solution of 87.5 mg of aminodextran (AMD; nominal molecular weight=40,000, approx. 6 amino groups per mole aminodextran; see U.S. Pat. No. 6,653,456) in 3.5 mL of dry DMSO (stirred 30 m for complete dissolution; concentration=25 mg/mL) at RT was added 13.9 mg of compound (6) [presentation ratio of derivative:AMD=8:1] dissolved in dry DMSO and the reaction stirred overnight at RT in a capped amber container. The reaction mixture was transferred to a dialysis cassette (Pierce Biotechnology Inc., Rockford, Ill.; SLIDE-A-LYZER Dialysis Cassette; 3,500 MWCO) and dialyzed sequentially against DMSO-water over several days with decreasing amounts of DMSO and several changes at each DMSO concentration, ending in dialysis against several changes of water alone. The retentate was removed from the cassettes, frozen and lyophilized to give AMD conjugate (22) as an amorphous solid which was stored at −20° C. until it was used.

Example 19

Preparation of Aminodextran Conjugates (23), (24), (25), and (26)

These were prepared in a similar manner as described in Example 18, all using a presentation ratio of derivative:AMD=8:1. Dialysis in a similar manner, and lyophilization of the final conjugate as described previously then gave AMD conjugates (23), (24), (25), and (26). as amorphous solids.

Example 20

Preparation of Phenobarbital Antibody Microparticles

Ten percent (w/v) latex microparticles (number of carboxy groups approx. 0.21 mmol/g latex, mean microparticle diameter 0.2 μm, Seradyne Inc., Indianapolis, Ind.) were diluted to one percent (w/v) concentration with 10 mM 2-morpholino-ethanesulfonic acid (MES), pH 5.3 containing 0.09% (w/v) ascorbic acid sodium salt. The desired volume of 1% microparticles was measured out and the microparticles activated by the addition of N-hydroxysulfosuccinimide (sulfo-NHS) followed by the addition of N-ethyl-N'-(3-dimethyl-amino-propyl)carbodiimide hydrochloride (EDC.HCl). Both sulfo-NHS and EDC were added at a ratio of 10 moles of each reagent per mole of carboxylates present on the surface of the microparticles. After stirring for about 1 hour at room temperature, the microparticles were washed, concentrated and resuspended to a concentration of 2% by exchange of buffers into 50 mM 3-morpholinopropanesulfonic acid (MOPS), pH 5.7, containing 0.09% (w/v) of ascorbic acid sodium salt, in a hollow-fiber system. A solution of phenobarbital monoclonal antibodies (MAK<Pheba>M-29D4-IgG) in 50 mM MOPS buffer, pH 5.7, also containing 0.09% (w/v) of ascorbic acid sodium salt and 10 g/L of BSA, was added to the resuspended microparticles such that there was 0.2 mg antibody/mL of microparticle solution. The antibody-latex mixture was stirred for about 1 hour at 23-27° C. A solution of 90 mg/mL of BSA in 50 mM MOPS, pH 5.7, containing 0.09% (w/v) of ascorbic acid sodium salt, was then added to the latex mixture (1.125 mg BSA/mg latex). After stirring for 0.5-1.5 hours at 23-27° C., a solution of 11% (w/w) 2-(2-amino-ethoxy)ethanol (AEO) in water adjusted to pH 9 with HCl, was added to the latex mixture. After stirring overnight at 40-45° C., the microparticles were washed with and exchanged into storage buffer (50 mM MOPS, pH 7.4, 0.1% (w/v) BSA, 0.09% sodium azide) to a final concentration of 1% latex microparticles (w/v) which was then stored at 2-8° C. until used.

Example 21

ONLINE Type-2 Assay (KIMS) with Conjugates of the Invention and Antibody using HITACHI Clinical Chemistry Analyzer and Construction of the Calibration Curves Assays were performed on Roche/Hitachi 917 clinical chemistry analyzers (Roche Diagnostics GmbH) at 37° C. The reaction mixtures (283 μL) contained 3 μL of a calibrator as described below or sample, PIPES disodium salt at 27.41 g/L, PIPES free acid at 2.99 g/L, sodium chloride at 14.612 g/L, PLURONIC F-127 at 0.49 g/L, anti-HAMA antibody (POLYMAK33: Roche Diagnostics GmbH) at 0.0124 g/L, sodium azide at 0.90 g/L, potassium thiocyanate at 4.81 g/L, bovine serum albumin (BSA) at 1.0 g/L, free phenobarbital at 0.0001 g/L, MOPS sodium salt at 3.81 g/L, MOPS at 1.73 g/L, polyacrylic acid (PAA) at 0.9% (w/v), microparticles as described in Example 20 at 0.04% (w/v), and phenobarbital-aminodextran conjugate as shown below:

| Phenobarbital-aminodextran conjugate | Concentration (g/L) |
|---|---|
| (22) | 0.00025 |
| (23) | 0.00025 |
| (24) | 0.00025 |
| (26) | 0.0003 |
| (25) | 0.00015 |

Calibration curves were constructed by using commercially available Roche TDM Multi-cal calibrator sets (Roche PRECISET TDM I calibrators, Part#03375790 190) containing phenobarbital at 0.0, 5.0, 10.0, 20.0, 40.0 and 60.0 mg/mL.

Assays were monitored spectrophotometrically by following the agglutination of microparticles at a wavelength of 600 nm. The calibration curves obtained using each of the phenobarbital-aminodextran conjugates are shown in FIG. 8, which shows the close similarity and near superimposability of the curve shapes obtained using the different conjugates.

Example 22

Phenobarbital Microparticle Immunoassay Study Using Negative Serum Samples

Five negative serum samples known to contain no phenobarbital were tested in the assay as described in Example 21 wherein they were placed into the analyzer sample cups and used as a sample. Each was tested in duplicate against the calibration curve obtained using the different phenobarbital-aminodextran conjugates (22), (23), (24), (25), and (26). The results obtained were as shown in the table below.

| Aminodextran conjugate | Samples from in-house draw | | | | |
| --- | --- | --- | --- | --- | --- |
| | #16 | #17 | #19 | #22 | #23 |
| (22) | 0.0 | 0.0 | 0.2 | 2.9 | 0.0 |
|      | 0.0 | 0.0 | 0.2 | 2.8 | 0.0 |
| (23) | 0.0 | 0.0 | 0.1 | 2.8 | 0.0 |
|      | 0.0 | 0.0 | 0.0 | 2.8 | 0.1 |
| (24) | 0.0 | 0.0 | 0.4 | 3.2 | 0.2 |
|      | 0.0 | 0.0 | 0.5 | 3.1 | 0.3 |
| (26) | 0.0 | 0.0 | 0.3 | 2.8 | 0.2 |
|      | 0.0 | 0.0 | 0.4 | 2.8 | 0.3 |
| (25) | 0.0 | 0.1 | 0.5 | 3.4 | 0.1 |
|      | 0.0 | 0.3 | 0.4 | 3.4 | 0.2 |

The results indicated whether there was a positive bias in the assay using the reagents of the assay, as the desired or theoretical results should be zero amount of phenobarbital being observed. The apparent concentrations of phenobarbital returned in the assay indicated that conjugates (22) gave the best overall results with values of zero or close to zero, (23) and (26) were acceptable, while conjugates (24) and (25) gave undesirable slightly higher values. In particular, the results using conjugate (25) were unexpected, as it was similar in structure to and possessed the hydrophilic DADOO moiety as found in conjugate (26).

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A phenobarbital analog having a structure

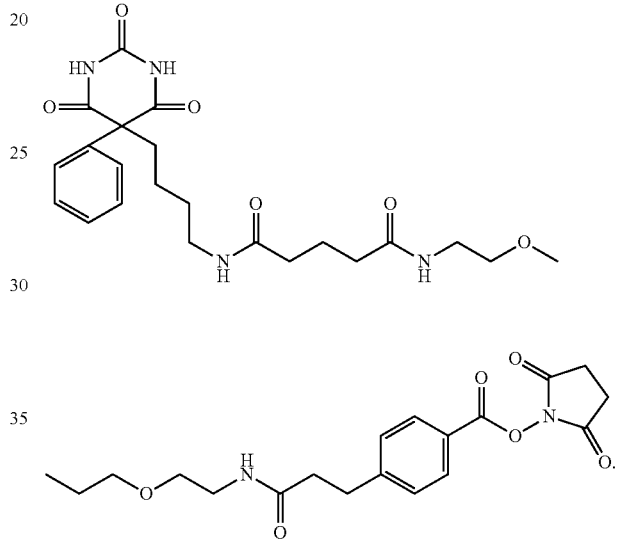

2. A phenobarbital analog having a structure

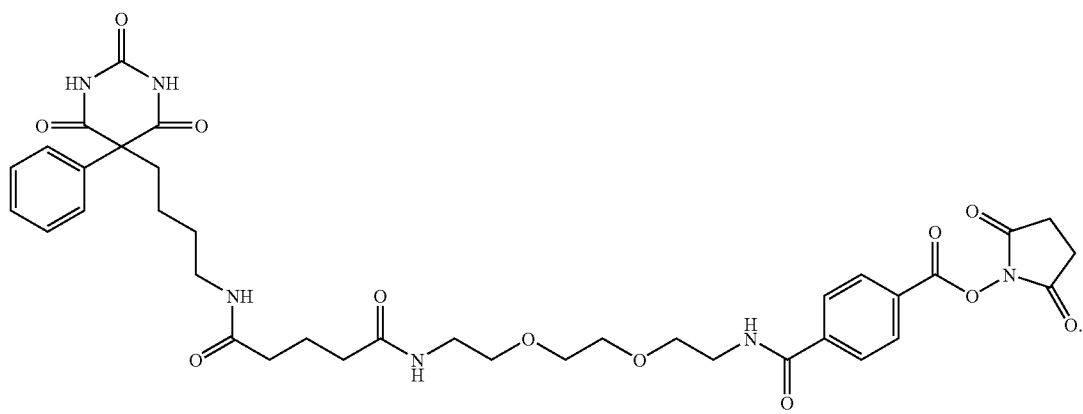

3. A phenobarbital analog conjugate having a structure
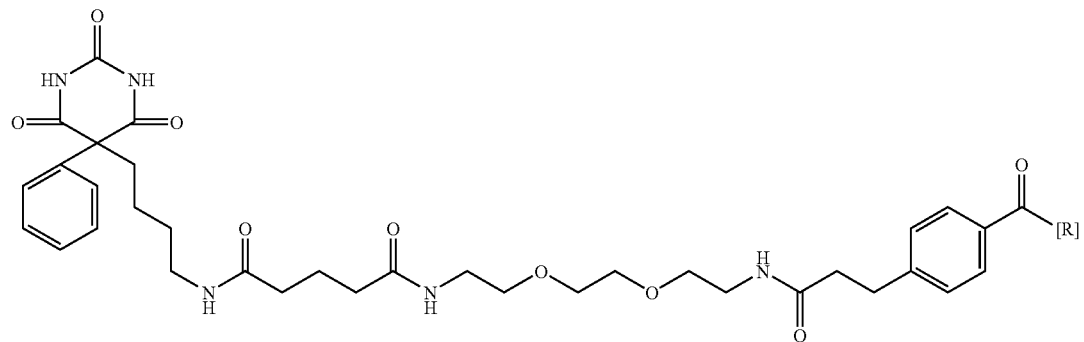
wherein R is aminodextran.
4. A phenobarbital analog conjugate having a structure
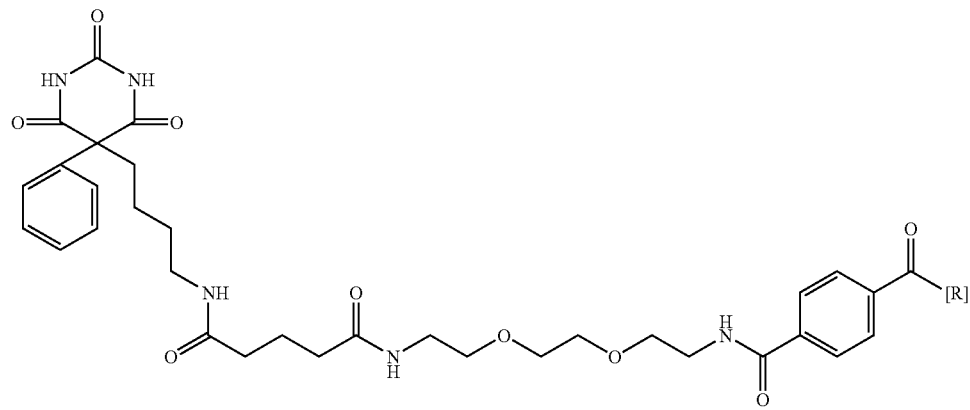
wherein R is aminodextran.
* * * * *